United States Patent [19]

Demers et al.

[11] Patent Number: 4,591,267

[45] Date of Patent: * May 27, 1986

[54] SPECTROMETER

[75] Inventors: Donald R. Demers, Nashua, N.H.; Charly D. Allemand, Newton, Mass.

[73] Assignee: Baird Corporation, Bedford, Mass.

[*] Notice: The portion of the term of this patent subsequent to Nov. 17, 1998 has been disclaimed.

[21] Appl. No.: 691,834

[22] Filed: Jan. 16, 1985

Related U.S. Application Data

[62] Division of Ser. No. 537,177, Sep. 29, 1983, which is a division of Ser. No. 254,929, Apr. 16, 1981, Pat. No. 4,432,644.

[51] Int. Cl.$^4$ .................... G01J 3/443; G01N 21/64; G01N 21/73
[52] U.S. Cl. .................................... 356/316; 356/317
[58] Field of Search ............... 356/315, 316, 317, 318, 356/417

[56] References Cited

U.S. PATENT DOCUMENTS

| | | | |
|---|---|---|---|
| 2,663,801 | 12/1953 | Slavin et al. | 356/417 X |
| 2,847,899 | 8/1958 | Walsh . | |
| 3,428,401 | 2/1964 | Buzza | 356/187 |
| 3,619,061 | 11/1971 | Mitchell | 356/85 |
| 3,699,383 | 10/1972 | Chaney | 313/209 X |
| 3,958,883 | 5/1976 | Turner | 356/85 |
| 4,293,220 | 10/1981 | Denton et al. | 356/316 |
| 4,300,834 | 11/1981 | Demers et al. | 356/316 |
| 4,326,802 | 4/1982 | Smith, Jr. et al. | 356/328 |
| 4,375,919 | 3/1983 | Busch | 356/328 |
| 4,432,644 | 2/1984 | Demers et al. | 356/316 |

FOREIGN PATENT DOCUMENTS 12432  3/1971  Japan .................. 356/315

OTHER PUBLICATIONS

Measures et al., "Analyzing Fluorescence Decay", *Lasar Focus*, Nov. 1974, pp. 49-52.
Mitchell et al., "Simultaneous Multielement Analysis Using Sequentially . . . ", Spectrochimica Acta, vol. 25B.
A. Montaser and V. A. Fassel, "Inductively Coupled Plasmas as Atomization Cells . . . ", *Analytical Chem.*, vol. 48, No. 11.
V. A. Fassel, "Quantitative Elemental Analyses . . . ", *Science*, vol. 202, Oct. 13, 1978, pp. 183-191.
V. A. Fassel and R. N. Kniseley, "Inductivity Coupled Plasma-Optical Emission Spectroscopy", *Analytical Chemistry*, vol. 46, No. 13, (Nov. 1974).
V. A. Fassel and R. N. Kniseley, "Inductively Coupled Plasma", *Analytical Chemistry*, vol. 46, No. 13, (Nov. 1974), pp. 1155A-1164A.
D. G. Mitchell, "Simultaneous Multi-Element Analysis . . . ", Technicon Ind. Congress, Nov. 2-4, 1970, NYC.
Lichte et al., *Analytical Chemistry*, vol. 52, No. 1, Jan. 1980, pp. 120-124.
Mavrodineanu et al., *Applied Optics*, vol. 7, No. 7, Jul. 1968, pp. 1281-1285.
Demers, *Applied Spectroscopy*, vol. 22, No. 6, Nov.-Dec. 1968, pp. 797 and 798.
Winefordner et al., *Applied Spectroscopy*, vol. 29, No. 5, Sep.-Oct., 1975, pp. 369-385.

*Primary Examiner*—F. L. Evans
*Attorney, Agent, or Firm*—Morse, Altman & Dacey

[57] ABSTRACT

A fluorescence spectrometer for multielement analysis including a source for atomizing a dispersed sample along an axis and a plurality of energizers and detectors preferably arranged in pairs about the source, with each of the pairs designed for analyzing one element. Preferably, the source is an inductively coupled plasma. Means is provided for each of the pairs to view a different segment of the source along its axis, depending on the element to be analyzed. Preferably, such means includes: a source movable along its axis; fiber optics interposed between the energizers and the source and between the source and the detectors; and a movable optical element interposed between the energizers and the source and between the source and the detectors. The spectrometer further features a polychromator for use in lieu of matched optical filters in the detectors and demountable hollow cathode lamps as energizers.

3 Claims, 10 Drawing Figures

SPECTROMETER

This is a division of application Ser. No. 537,177 filed on Sept. 29, 1983, which is a division of Ser. No. 254,929 filed Apr. 16, 1981, now U.S. Pat. No. 4,432,644.

BACKGROUND OF THE INVENTION

1. Field of the Invention

The present invention relates generally to fluorescence spectometers and, more particularly, to an inductively coupled plasma atomic fluorescence spectrometer for the multielement analysis of samples.

2. The Prior Art

Until the early 1960's, general purpose atomic spectroscopy measurements had been carried out by using flame atomic emission (FAE) instruments. FAE instruments employ no external excitation source. Rather, in FAE instruments the free atoms are excited by thermal collision with high energy species of the atomization source (e.g., the flame gas atoms), and a portion of the excited atoms undergoing radiational deactivation is measured. In atomic emission (AE) spectroscopy, all of the possible energy levels above the ground state of a given element are populated and all of these excited levels are undergoing radiational deactivation. Consequently, AE spectra are spectral-line rich, particularly where the sample analyzed contains more than one element.

In the 1960's, flame atomic absorption spectroscopy (FAAS) instruments came increasingly into use. These FAAS instruments employ a separate excitation source, such as a hollow cathode lamp, for each element being analyzed in a sample, in addition to the flame and the monochromator used in an FAE instrument. In flame atomic absorptin (AA) spectroscopy, the atomization source (i.e., the flame) functions primarily to dissociate a sample into its constituent atoms and to leave the latter in their lowest energy state, i.e., the ground state of energy level. It is the function of the separate excitation source in AA spectroscopy to excite some of these free atoms in the ground state to a higher state of energy level. In so doing, these atoms absorb some of the excitation source radiation, and the fraction absorbed, relative to when there are no atoms of the element analyzed for present in the atomization source, is indicative of the concentration of that element in the sample. In an AA instrument, the resultant spectra are unambiguous and simple since each element absorbs best at its characteristic wavelength. The signal observed at this characteristic wavelength is indicative of the concentration of that element in the sample. In an AA instrument, however, the radiation from the separate excitation source, the atomization source and the detector are all required to be mounted along the same axis. Because of this constraint, it is extremely difficult to design any multichannel AA instrument for multielement analysis. Consequently, multielement AA analyses are carried out sequentially on single channel AA instruments.

No such constraint exists in atomic fluorescence (AF) spectroscopy. In contrast to AA spectroscopy, in AF spectroscopy the excitation source can be mounted anywhere off the atomization source-detector axis. Most AF spectroscopic instruments arrange the excitation source and the detector at right angles to each other and in a horizontal plane when viewing the isotropically emitted fluorescence radiation from the analyte in the atomization source. Consequently, designing a multichannel AF instrument for multielement analysis is inherently simpler than with AA. Furthermore, it is a characteristic of AF that the AF spectra are simple, as in AA.

During the 1970's, a promising new atomization source emerged—the inductively coupled plasma (ICP). A plasma is defined as a luminous gas, a significant fraction of whose atoms or molecules is ionized. Plasmas therefore are considered to be gaseous conductors. As such, plasmas readily interact with magnetic fields, making it possible to couple a plasma to a high frequency power source. The emergence of the inductively coupled plasma (ICP) led to the widespread use of ICP-Atomic Emission Spectroscopy (AES) systems, particularly in the simultaneous multielement analysis (SMA) for many trace elements. For unlike in AA and in AF spectroscopy, in an ICP-AES system, no separate excitation source for each element being analyzed is required. Consequently, SMA can be done in a relatively simple manner.

An ICP-AES system, however, suffers from a serious disadvantage and that is the problem of spectral line interference. This problem of spectral line interference is particularly severe when analyzing a sample for traces of metals in the presence of other metals such as tungsten, cerium, uranium, iron, vanadium and the like. It has been found that these and many of the transition series metals as well as all of the lanthanide series metals are spectral-line rich in the 220–420 nm wavelength region commonly employed in a typical ICP-AES analysis. As a consequence, any ICP-AES system must include a high resolution spectrometer. Nonetheless, an ICP-AES analysis of a sample containing a number of metals at concentrations above their respective detection levels still exhibits numerous instances of overlap of the emission lines of the elements present in the sample. The analyst then has to unravel which fraction, if any, of the total measured atomic emission signal in each channel is from an intended element and which fraction (or fractions) is (or are) from an interfering element (or elements). Slit changes and the use of computers to help disentangle the overlay are required to produce reliable and accurate results. Furthermore, the bandwidth of the atomic emission line in the wings in ICPs (and also in flames) can be 0.5 Angstroms or more. Thus, the designing of a spectrometer with a resolution better than 0.5 Angstroms, while reducing the number of instances of spectral line overlap interferences, would still not eliminate them. The problem of spectral line overlap interference, therefore, is and remains a fundamental limitation to the employment of ICP-AES systems.

The problem of spectral line overlap interference has been effectively met by the provision of an inductively coupled plasma atomic fluorescence spectrometer (ICP-AFS) system disclosed in copending application Ser. No. 152,387, Demers et al, filed May 22, 1980. The ICP-AFS system of application Ser. No. 152,387 comprises a plasma source for atomizing a dispersed sample and directed along a central axis, a plurality of replaceably mounted optical stations surrounding the central axis, each including an energizing illuminator and a fluorescence detector focused at the same region of the plasma stream, and a readout system for identifying the unknown samples. The fluorescence detector includes an optical interference filter matched to the characteristic radiation of its associated energizing illuminator, and the readout system incorporates multiplexing and intermittent modulation of the energizing illuminators.

The ICP-AFS system of application Ser. No. 152,387, effective as it is in substantially eliminating spectral line overlap interference, nevertheless exhibits some shortcomings. For one, the physical size of the optical stations places a limit on the number of channels that can be built into the system, thus limiting the number of elements that can be analyzed thereby. For another, the required presence and structure of certain of the components adds to the cost and complexity of the system. These include: use of a specific optical interference filter and expensive hollow cathode lamps and photomultiplier tubes for each element being analyzed. For still another, adjustment of the optical stations for optimum observation heights is awkward in that it requires the loosening of screws, followed by tilting of the particular station about a pivot axis and then retightening the loosened screws. For still another, since the plasma source has been operated at a lower forward rf power, its operation required careful attention lest it became extinguished upon the introduction of sample aerosol into it, with some of the elements not being efficiently volatilized, resulting in some matrix interferences.

SUMMARY OF THE INVENTION

It is a principal object of the present invention to overcome the above shortcomings by providing an improved fluorescence spectrometer for the simultaneous multielement analysis of unknown samples.

More specifically, it is an object of the present invention to provide a fluorescence spectrometer for the simultaneous multielement analysis (SMA) of samples comprising a source for atomizing a dispersed sample along an axis and a plurality of energizers and detectors, preferably arranged in pairs about the source, with each of the pairs designed for analyzing one element. Preferably, the source is an inductively coupled plasma operated at a higher rf power and with an active observation height shifted higher in an axially enlarged and hotter plasma discharge. Means is provided for each of the pairs to view a different segment of the source along its axis, depending on the element being analyzed by the particular pair. Preferably, such means includes: a source designed for limited axial displacement; movable fiber optics interposed between the energizers and the source and between the source and the detectors; and a movable optical element interposed between the energizers and the source and between the source and the detectors. Preferably, the energizers are demountable hollow cathode lamps and a monochromator is employed in lieu of the optical interference filters.

The resultant fluorescence spectrometer of the invention is able spatially to accommodate almost any number of channels such as from a practical point of view may be desired. Furthermore, adjustment of the optical stations for respective optimum observation heights of the plasma source has been greatly facilitated and simplified. Still further, by employing higher rf power for the plasma source and by shifting higher the observation height in the plasma, a more efficient and a more stable ICP-AFS system has been achieved whose matrix interference has been lowered to a level so as to rival in performance that of the ICP-AES technique.

Other objects of the present invention will in part be obvious and will in part appear hereinafter.

The invention accordingly comprises the ICP-AFS system of the present disclosure, its components, parts and their interrelationships, the scope of which will be indicated in the appended claims.

BRIEF DESCRIPTION OF THE DRAWINGS

For a fuller understanding of the nature and objects of the present invention, reference is to be made to the following detailed description, which is to be taken in connection with the accompanying drawings, wherein.

DETAILED DESCRIPTION OF THE PREFERRED EMBODIMENT

Figure 1:
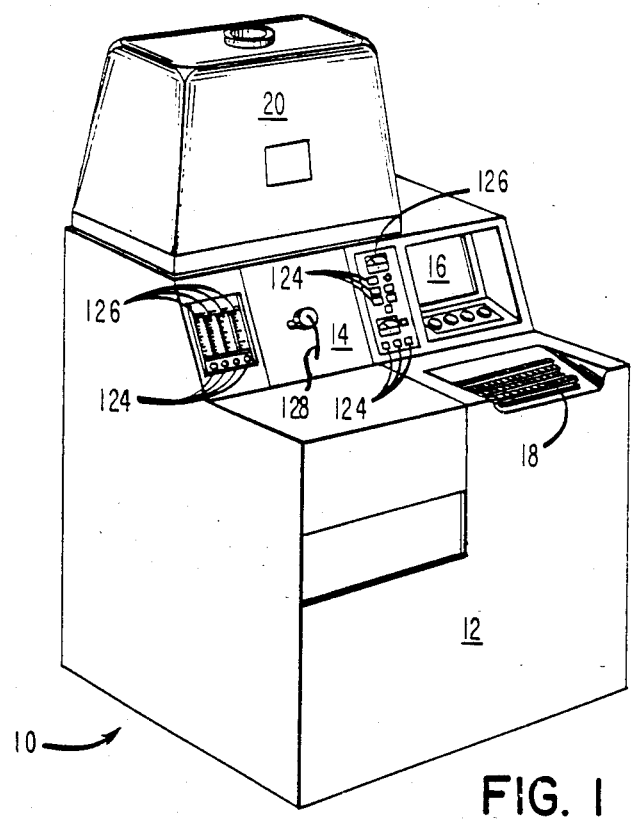
FIG. 1 is a perspective view of an ICP-AFS instrument constructed in accordance with the present invention.

A perspective view of an inductively coupled plasma atomic fluorescence spectrometer (ICP-AFS) instrument 10 constructed in accordance with the present invention for the simultaneous multielement analysis (SMA) of unknown samples in solution is illustrated in FIG. 1. Preferably, the ICP-AFS instrument 10 is of a floor-mounted type that includes a base cabinet 12, featuring an instrument panel 14, a CRT display 16, a keyboard 18, and an overhead container 20. Most of the instrumentation is housed in the base cabinet 12, while the optics, surrounding a suitable atomization source 22, are essentially contained within the overhead container 20, observe FIG. 2. Preferably, the atomization source 22 is a plasma stream controlled by inductive coupling to a radio frequency (rf) generator of the type disclosed in U.S. Pat. No. 3,958,883 issued May 25, 1976 to Arthur S. Turner and assigned to the assignee of the present application. The teachings of this U.S. Pat. No. 3,958,883 regarding rf generators are incorporated herein by reference. Such an rf generator forms part of the instrumentation that is housed in the base cabinet 12. Alternatively, the atomization source 22 can be a flame, an electrochemical atomizer or other type of plasma not necessarily controlled by radio frequency.

In general, the fluorescence spectrometer 10 comprises, in addition to the source 22, a plurality of energizers 24 and a plurality of fluorescence detectors 26 preferably arranged in pairs about the source 22, with each one of the pairs designed for analyzing one element. Means is provided for each of the pairs to view a different segment of the source 22 along its axis 28, depending on the particular element to be analyzed. As known, different elements, particularly different classes of elements, possess different physical properties. Because of their different physical properties, these different elements require different temperatures for them to be efficiently dissociated (volatilized) into the ground state. The plasma stream 22 exhibits different temperature gradients along its axis 28, with the highest temperature being at the lowest part of the stream 22 and the lowest temperature being at the top of the stream 22. Consequently the easily dissociated elements are analyzed by pairs of energizers 24 and detectors 26 viewing a higher segment of the plasma stream 22, as illustrated on the right-hand side in FIG. 2. In contrast, the more difficult to dissociate elements are analyzed by pairs of energizers 24 and detectors 26 viewing a lower segment of the plasma stream 22 where the temperature is higher, as illustrated on the left-hand side in FIG. 2. In order to achieve a more efficient and more stable ICP-AFS system 10, the plasma stream 22 preferably is operated at a higher forward rf power than was the case with respect to the instrument disclosed in copending application Ser. No. 152,387, mentioned above. The preferred rf power for the ICP-AFS system 10 is from about 350 to about 600 Watts at forty Megahertz. This preferred rf power contrasts with a forward rf power of from about 500 to about 800 Watts at twenty-seven Megahertz utilized in the instrument of copending application Ser. No. 152,387. The resultant plasma stream 22 is larger and hotter than before and much more efficient in volatilizing the dispersed elements introduced therein. The plasma stream 22 is also easier to operate since it will not extinguish when introducing the sample aerosol into it. Further, if the instrument designer wants it, a smaller rf generator can be utilized and still achieve about as much rf power in the plasma stream 22 as before with a larger rf generator. Since the sample aerosol is traveling in a higher temperature zone due to the larger and hotter plasma stream 22 as a result of the higher rf power put into the plasma stream 22, a more efficient volatilization of the elements occurs. Due to this improved efficiency, matrix interferences have been materially reduced. The level of matrix interferences is so low as to favorable compare with that achievable with an ICP-AES technique. In addition to improved efficiency in volatilizing elements, there has been also a shift higher in the effective observation height in the plasma stream 22 than was the case in the instrument disclosed in the copending application Ser. No. 152,387. Because of this shift higher in the effective observation height in the plasma stream 22, as will be more fully described below, the atomization source background signal ($I_b$) has been reduced even further. Reduction in the atomization source background signal, in turn, results in further improvement in the signal to noise (S/N) ratio for the ICP-AFS instrument 10 of the invention.

Figure 2:
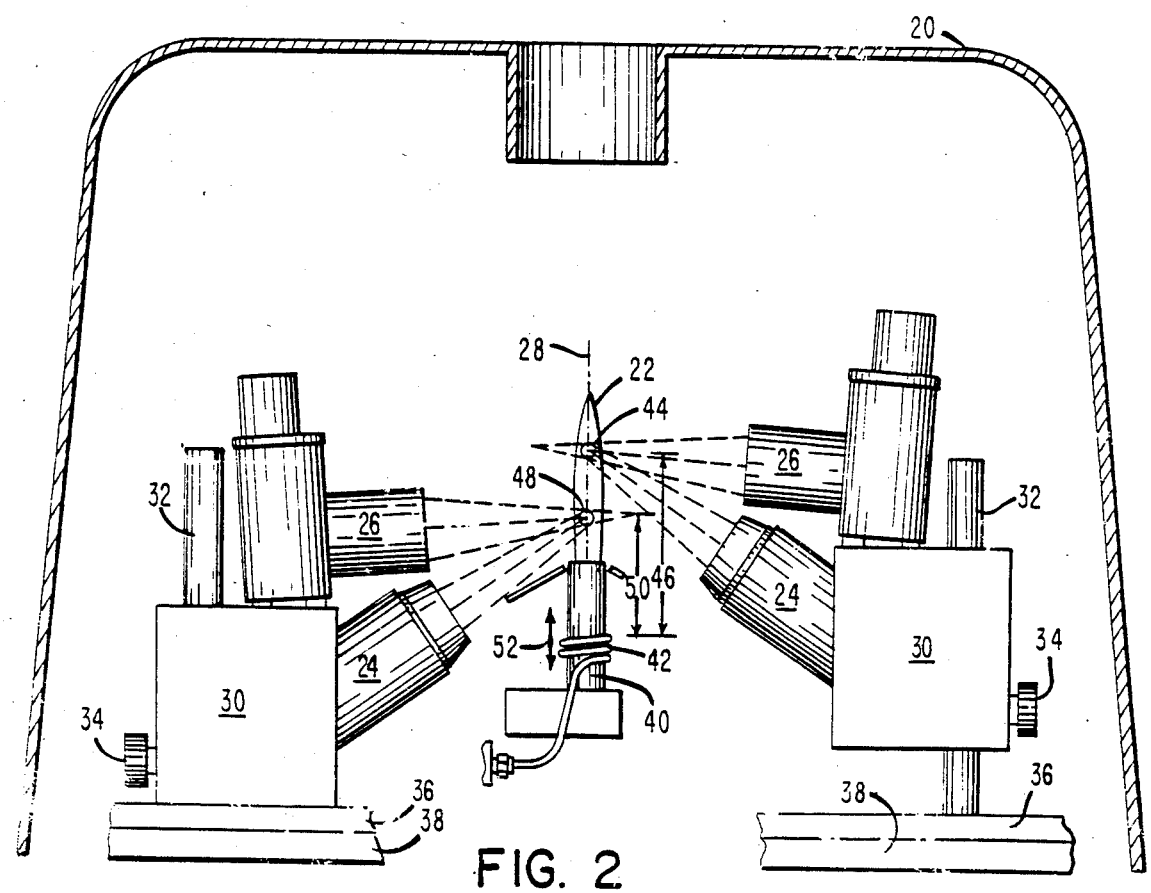
FIG. 2 is a front elevation of one preferred embodiment of a portion of the ICP-AFS instrument shown in FIG. 1.

The means provided for each of the pairs of energizers 24 and detectors 26 to view a defferent segment of the plasma stream 22 along its axis 28 can take any one of the following forms. The arrangement depicted in FIG. 2 is similar to that disclosed in copending application Ser. No. 152,387. As shown in FIG. 2, a pair comprising one energizer 24 and one detector 26 is mounted in a suitable housing 30. The housing 30 is vertically displaceable along a post 32 and is secured to the post 32 by means of a set screw 34. The post 32 is also provided with a base 36 which is bayonet-like mounted to a support 38 forming part of the overhead container 20. By adjusting the height of the respective housing 30 on its post 32, the particular segment of the plasma stream 22 being viewed by that particular pair of energizer 24 and detector 26 is determined.

As will be observed, the plasma stream 22 emanates from a plasma torch 40, which is surrounded by an induction coil 42. Coil 42 in turn is connected to an rf generator, not shown, which delivers a tuned and matched rf power to the plasma stream 22. As mentioned, the function of the plasma stream 22 is simply to atomize the sample so as to produce a large ground state population of the sample. It is not a function of the plasma stream 22 also to excite this ground state population to higher energy levels, as is the case in an ICP-AES instrument. As noted in FIG. 2, the right-hand pair is positioned to view a segment 44 of the plasma stream 22. This segment 44 is about five to six mm in diameter. The center of this segment 44 is about 140 mm above the top turn of the induction coil 42, as indicated by the size of the arrow 46. This pair is thus positioned and designed to detect easily to be dissociated elements, such as mercury (Hg) or arsenic (As). The left-hand pair of energizers 24 and detector 26, on the other hand, is positioned to view a segment 48 located much lower in the plasma stream 22. This segment 48 is also about five to six mm in diameter. The center of this segment 48 is about 75 mm above the top turn of the induction coil 42, as indicated by the size of the arrow 50. This left-hand pair is thus positioned and designed to detect the more difficult to be dissociated elements that require a higher temperature, such as aluminum (Al) or tin (Sn). For the detection of certain other elements in the sample, the following observation heights in the plasma stream 22 have been optimized: (a) for the alkali metals, such as sodium (Na), potassium (K) and lithium (Li), a segment whose center is about 85 mm above the top turn of the induction coil 42; (b) for the alkaline earths, such as strontium (Sr), calcium (Ca) and magnesium (Mg), as well as the transition metal chromium (Cr), a segment whose center is about 105 mm above the top turn of the induction coil 42; and (c) for some metallic elements, including copper (Cu) and zinc (Zn), a segment whose center is about 120 mm above the top turn of the induction coil 42.

In addition to having the housing 30 vertically displaceable along the post 32, the means for the pairs of energizers 24 and detectors 26 to view a different segment of the plasma stream 22 along its axis 28 includes a second arrangement also depicted in FIG. 2. This second arrangement takes the form of the plasma stream 22 itself being movable along its axis 28 by so constructing the plasma torch 40 as to be vertically displaceable, as indicated by the arrow 52. Either arrangement alone or if preferred in combination, can be used to select the particular segments of the plasma stream 22 that the respective pairs of energizers 24 and detectors 26 are to view.

Figure 5:
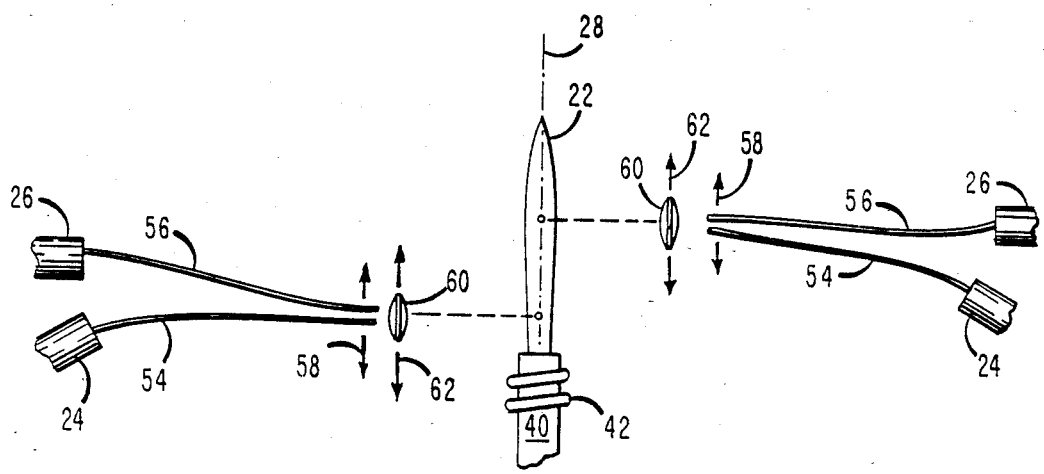
FIG. 5 is a schematic illustration of a second preferred embodiment of a portion of the ICP-AFS instrument shown in FIG. 1.

A further means for the pairs of energizers 24 and detectors 26 is illustrated in FIG. 5. This means essentially comprises fiber optics interposed between the energizers 24 and the plasma source 22 and between the plasma source 22 and the detectors 26. As shown in FIG. 5, a pair of sheathed fiber optics 54 and 56 are optically coupled at one end to the energizers 24 and the detectors 26, respectively. At the other end, the sheathed fiber optics 54 and 56 are displaceable along the axis 28 of the plasma source 22, as indicated by the arrows 58. These sheathed fiber optics 54 and 56 collect the light from the energizers 24 and transfer it to the plasma source 22 and, in like fashion, collect the atomic fluorescence from the plasma source 22 and transfer it to the detectors 26. A comparison of FIGS. 2 and 5 readily discloses that the energizers 24 and the detectors 26 are farther removed from the plasma atomization source 22 when employing the sheathed fiber optics 54 and 56 than without them. In fact, one of the practical limitations on the number of channels, i.e., the number of elements to be analyzed, that can be built into one ICP-AFS instrument 10 as shown in FIG. 2 has been the number of such pairs of energizers 24 and detectors 26 that could be spatially accommodated around the plasma atomization source 22. By employing the sheathed fiber optics 54 and 56, the energizers 24 and the detectors can be located almost anywhere on the instrument 10, far away from the plasma source 22. Consequently, more channels can now be built into the ICP-AFS instrument 10 than heretofore practicable. In fact, the ICP-AFS instrument 10 as illustrated in FIG. 5 can be built with as many channels as desired. The utilization of the sheathed fiber optics 54 and 56 also permits a much easier selection and adjustment of the optimum observation heights for the respective pairs of energizers 24 and detectors 26 along the axis 28 of the plasma source 22 than is the case with the arrangement depicted in FIG. 2. Furthermore, a very efficient collection of both the excitation source light from the respective energizers 24 and the atomic fluorescence radiation from the plasma stream 22 is now possible. This is so because the optical fibers can be placed very close to both the excitation source and to the plasma. Consequently, significantly better detection limits are now achievable. As a further variation, the instrument illustrated in FIG. 5 can be built with but one detector 26. When employing one detector 26, atomic fluorescence radiation emanating from the plasma stream 22 and collected and transmitted by each and every one of the sheathed fiber optics 56 is transmitted, seriatim, to the one detector 26 only. The resultant instrument employing but one detector 26 is of necessity somewhat slower in operation than one using a separate detector 26 per each channel; it is, however, a simpler and less costly instrument.

A second arrangement of a means for facilitating each of the pairs of energizers 24 and detectors 26 to view a different segment of the plasma stream 22 along its axial length 28 is shown in FIG. 5 by the provision of a movable optical element 60. The optical element 60 shown is a lens. However, a mirror can likewise be used in lieu of the lens. The optical element 60 is interposed between the energizers 24 and the plasma source 22 and between the source 22 and the detectors 26. It is pointed out that the optical element 60 can be employed in conjunction with the sheathed fiber optics 54 and 56, as shown, or, in the alternative, without the fiber optics 54 and 56. The optical element 60 is movable, as indicated by the arrow 62, so as to allow either the energizers 24 or the detectors 26 or both to view a different segment of the plasma stream 22, i.e., to vary the optimum observation height of the plasma. Preferably, one separate optical element 60 is provided for each pair of energizers 24 and detectors 26.

Figure 8:
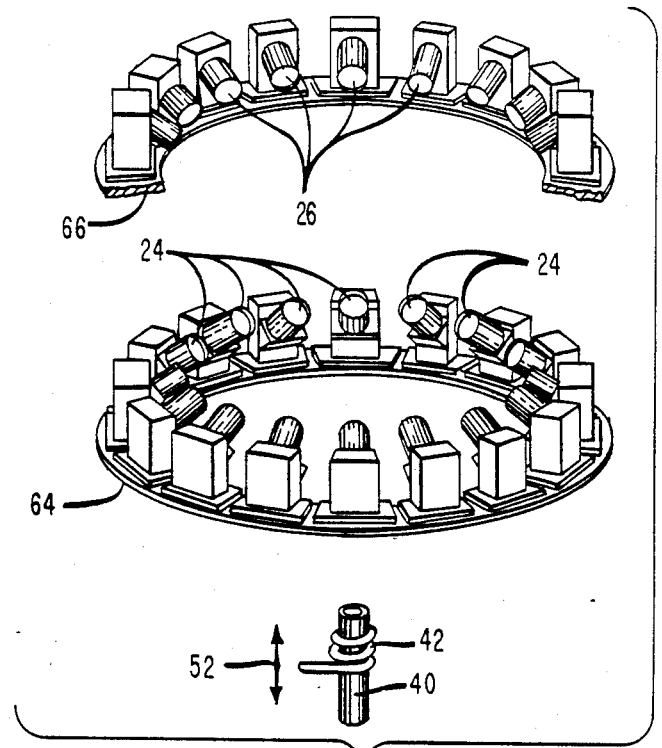
FIG. 8 is a perspective view of a fourth embodiment of a portion of the ICP-AFS instrument shown in FIG. 1.

FIG. 8 depicts a structural variation in the mounting of the energizers 24 and the detectors 26 in the ICP-AFS instrument 10. As shown in FIG. 2, each pair of energizers 24 and detectors 26 is mounted as a separately removable module or optical station. In contrast, the arrangement depicted in FIG. 8 is of a carousel-like mounting, with all of the energizers 24 mounted on one carousel 64 and all of the detectors 26 mounted on another carousel 66. When the two carousels 64 and 66 are assembled with respect to one another and about the plasma torch 40 by suitable support means, not shown, the energizers and the detectors 26 are porperly paired so that one pair will once again be directed to view a specific segment of the plasma stream 22 emanating from the plasma torch 40. In this arrangement, the adjustment for the optimum observation heights of all the pairs of energizers 24 and detectors 26 can only be effected together by moving the plasma torch 40 axially as indicated by the arrow 52.

Figure 3:
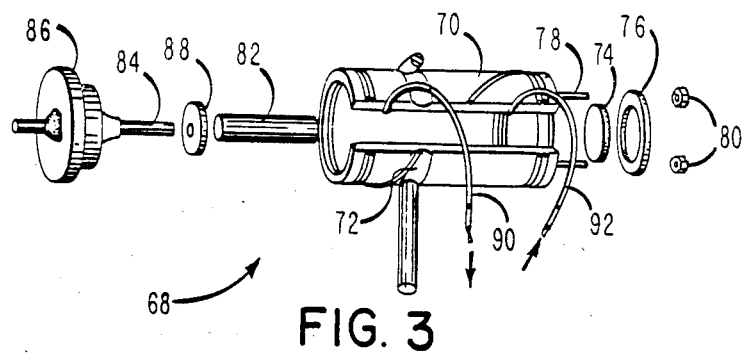
FIG. 3 is a perspective exploded view of a preferred demountable hollow cathode lamp.
Figure 4:
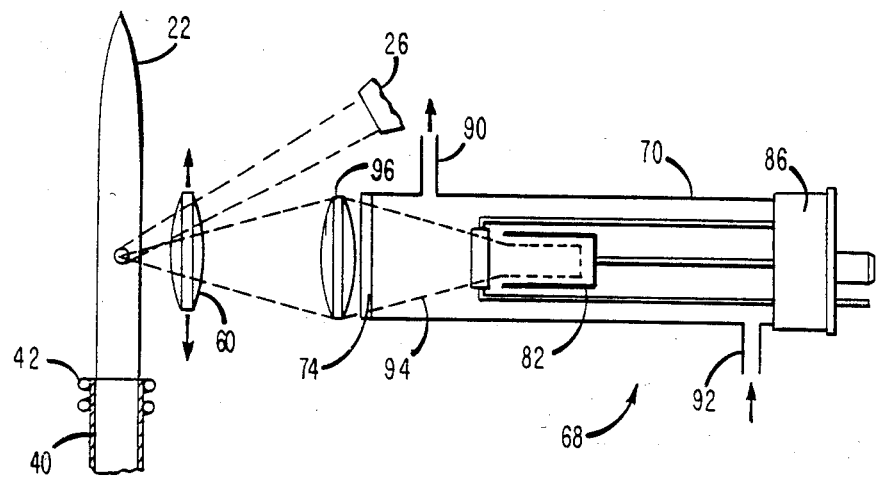
FIG. 4 is a schematic view of the demountable hollow cathode lamp of FIG. 3 and shown in operative association with a plasma source, a portion of a detector and a movable optical element interposed between the source and the detector.

As mentioned, the energizers 24 are hollow cathode lamps, preferably demountable hollow cathode lamps. A perspective exploded view of such a preferred demountable hollow cathode lamp 68 is shown in FIG. 3. Demountable hollow cathode lamp 68 basically comprises a cylindrical housing 70, about whose outer surface is mounted an anode 72. At the front, a disk 74 closes off the housing 70 and is held there in place by a suitable ring 76 secured to the housing 70 by bolts 78 and nuts 80. The cathode preferably is formed of a graphite rod 82 formed with a cavity at its forward end designed to contain a small amount, about 50 mg, of a particular metallic element, such as copper, aluminum or the like. The particular metallic element forms the cathode material and determines the characteristic radiation emitted by the particular demountable hollow cathode lamp. Preferably, the metallic element is introduced into the cavity of the graphite rod 82 in the form of metal cuttings or powder. The graphite cathode 82 is mounted on a cathode holder 84 whose base 86 is insulated from the cathode 82 by a suitable silica disk 88. If desired, the housing 70 can be cooled externally by recirculating water. When assembled, the demountable hollow cathode lamp 68 preferably is operated under reduced pressure, about $10^{-1}$ torr, in the presence of an inert gas such as argon or helium. It is this reduced pressure, a vacuum, which holds the base 86 and the cathode holder 84 to the housing 70. Relieving the vacuum permits the lamp 68 to be disassembled so that the graphite rod 82 containing one particular cathode material, say copper, can be changed quickly to another containing another cathode material, say aluminum. Once the hollow cathode rod 82 has been replaced, the housing 70 is once again evacuated of air and filled with an inert gas. Evacuation preferably is effected via a tube 90 and the inert gas is introduced through another tube 92. A further advantageous feature of utilizing the demountable hollow cathode lamp 68 resides in that it can be continuously flushed by the fill gas. As a consequence of such continuous flushing, undesirable deposition of cathode material on the front disk 74 is avoided. It is, of course, appreciated that such deposition affects the performance of the lamp 68 in that it reduces the amount of radiation emanating from the lamp 68 and being thus available for excitation of sample atoms in the plasma stream 22. Since deposition is avoided by flushing, the hollow cathode rod 82 can be positioned very close to the front disk 74, observe FIG. 4. As a result, a larger solid angle 94 of the radiation emitted from the lamp 68 can be collected and focused by an optical collecting element 96 on the plasma stream 22. This in turn further improves the detection limits of the ICP-AFS instrument 10 by enhancing its S/N ratio. The movable optical element 60 can also be incorporated here for adjusting the optimum observation height. It is also appreciated that it is far less expensive to replace the hollow graphite rod 82 than having to replace the entire hollow cathode lamp 68. Consequently, demountable hollow cathode lamps can be, and frequently are, pulsed to much higer currents in order further to enhance its radiation output, and thus the detection limits of the ICP-AFS instrument 10.

As mentioned, the fluorescence detectors 26 preferably comprise photomultiplier tubes. These photomultiplier tubes must of necessity incorporate some kind of filters, be they inexpensive color glass filters or more expensive optical interference filters. For each pair of energizers 24 and detectors 26, these filters must be matched to the characteristic radiation of its associated particular energizer 24, i.e., the hollow cathode lamp, regular or demountable. The embodiment depicted in FIG. 6 obviates the need of employing matching optical absorptive filters in each pair of energizers 24 and detectors 26. In lieu of all these optical absorption filters, a grating polychromator is used at the fluorescence radiation collecting part of the ICP-AFS instrument 10. As will be observed, fluorescence radiation 100 emanating from excited atoms in the plasma stream 22 is focused by the movable optical element 60 into an entrance slit 102 of the polychromator 98.

Atomic fluorescence spectra as produced by hollow cathode lamps, both regular and demountable, comprise only a few lines per atomized element in the plasma source 22. As a consequence, much wider spectrometer slits (both entrance and exit slits) can be used in the ICP-AFS instrument 10 than is possible with atomic absorption and atomic emission systems. Thus, the entrance slit 102 can have about a 4 nm bandpass as opposed to a previously required slit width of about $\leq 0.1$ nm. In the same fashion, the exit slits 104 are likewise wide, i.e., of a bandpass of about 4 nm. With wide exit slits 104 like these, the slits 104 can be positioned about the focal curve 106 without alignment problems. It suffices simply to mark the spots along the focal curve 106 where the respective manganese (Mn), magnesium (Mg), copper (Cu), zinc (Zn), sodium (Na), lead (Pb), etc., slits and their respective fluorescence detectors 108 should be located. As a consequence, a larger number of channels can be accommodated and a greater element selectability at less incremental cost can be achieved than heretofore possible. This latter advantage is due to the fact that additional optical interference filters for each additional element are avoided, as already mentioned above. Despite the employment of wide entrance 102 and exit slits 104, the resultant ICP-AFS instrument 10 still retains the ruggedness feature of a filter atomic fluorescence instrument. In addition, the resultant polychromator 98 is of a relatively small size, about 30 to 35 cm as opposed to one meter size for an emission polychromator.

The embodiment shown in and just described with reference to FIG. 6 incorporates a further advantageous feature: the employment of a vibrating refractor plate 110, preferably formed of quartz or the like. The plate 110 can be positioned adjacent the entrance slit 102, substantially as shown, or a plurality of such vibrating refractor plates can be positioned adjacent the exit slits 104, not shown. The operation and function of the vibrating refractor plate 110 is best described with reference to FIG. 7. As the quartz plate 110 is vibrated, note the arrow 112, its refractive index will effect a lateral shift of the dispersed spectrum as it passes through the plate 110. The extent of this shift is dependent on the angle at which the incident radiation strikes the plate 110, the thickness of the plate 110, and the refractive index of the plate 110. By vibrating the plate 110, the angle of incidence is changed and the output spectrum is shifted by an amount porportional to the extent and direction of the change. Thus, the refractor plate 110 can be used selectively to shift the spectrum across a slit 114 (or striking a grating 116, see FIG. 6) so that a particular wavelength or wavelengths can be quickly and precisely selected. The employment of the vibrating refractor plate 110, in conjunction with the grating polychromator 98, permits background correction at wavelengths adjacent the analyte spectral lines. More specifically, the refractor plate 110 corrects for light scattering interferences, i.e., the scattering of light by non-volatilized particles in the atomization source 22 into the detectors 108. The scattered signals result in false positive atomic fluorescence signals, which can be significant when relatively cool (i.e., non-ICP) sources are used. With the refractor plate 110 in place, the ICP-AFS instrument 10 can be operated under conditions which provide better detection limits for the instrument 10 without concern for any scattered light possibly resulting from the use of such conditions.

Figure 9:
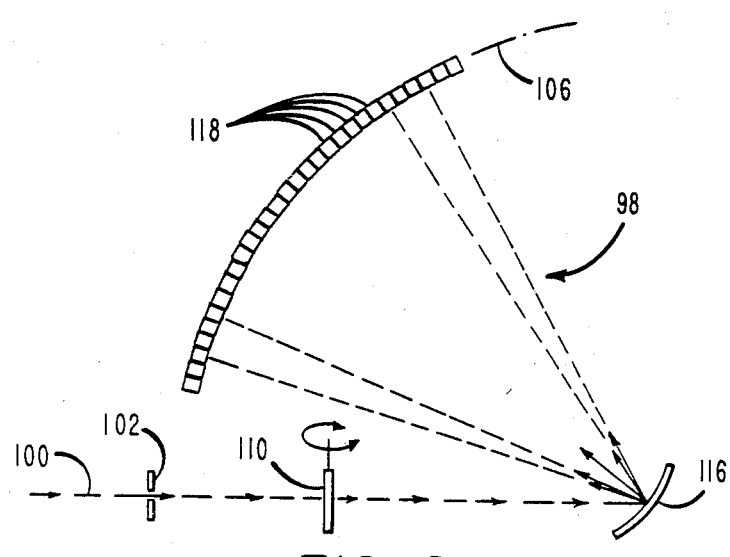
FIG. 9 is a schematic illustration of a fifth embodiment of a portion of the ICP-AFS instrument shown in FIG. 1.

The embodiment illustrated in FIG. 9 adds a further feature to the arrangement shown in and described with reference to FIG. 6. In FIG. 9, the fluorescence detectors 108 have now been combined with a diode array (or in the alternative with a TV-type display) to place a plurality of combination detectors and diodes 118 at the focal curve 106 of the polychromator 98. The employment of such a combination of detectors and diodes 118 (or TV-type display) provides a simultaneous, visual display of all signals and of the entire background spectrum at the CRT display 16 of the instrument 10, see FIG. 1. This simultaneous, visual display in turn allows for rapid and easy observation of the effects of sample matrix and instrument parameter changes.

It is again pointed out that the use of the optical element 60, be it a lens as shown or a mirror, together with the polychromator 98, permits the instrument 10 to view different segments of the plasma stream 22 along its axis 28. When using the optical element 60 together with the polychromator 98, it is preferred to analyze sequentially by groups of elements. For instance, first the easily dissociated but hard to ionize elements, such as zinc (Zn), copper (Cu), lead (Pb), iron (Fe) and the like are determined (e.g., analyzed) simultaneously at one observation height in the plasma stream 22. This is then followed by the simultaneous determination, at another observation height in the plasma stream 22, of the refractory elements, such as titanium (Ti), vanadium (V), boron (B), tungsten (W) and the like. Finally, and as a third group of elements, the easily dissociated and easily excited elements, such as the alkali metals like sodium (Na), potassium (K) and lithium (Li) and the like are determined simultaneously at still another observation height in the plasma stream 22.

Figure 6:
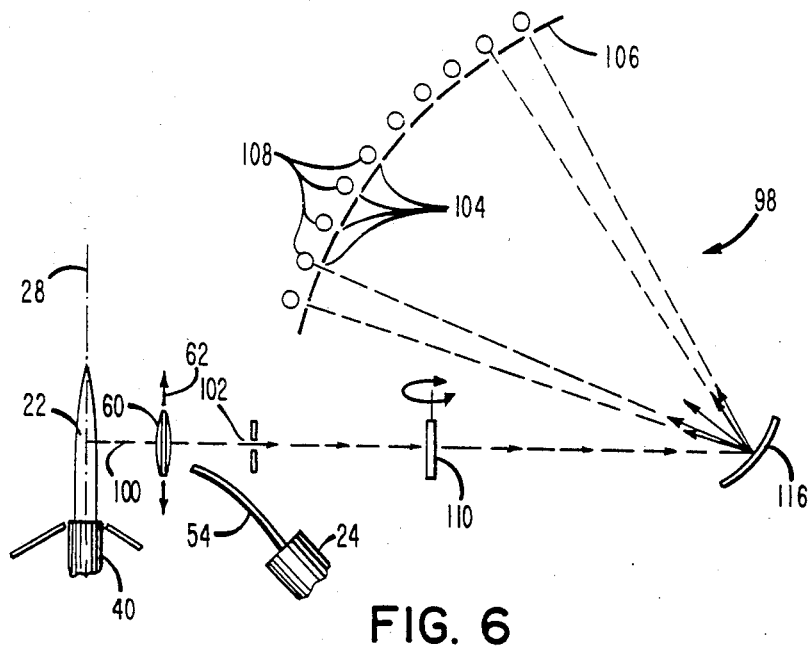
FIG. 6 is a schematic illustration of a third preferred embodiment of a portion of the ICP-AFS instrument shown in FIG. 1.
Figure 7:
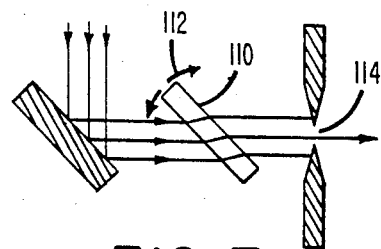
FIG. 7 is a schematic illustration of the operation of a part of the embodiment shown in FIG. 6.

As a further variation of either the embodiment shown in FIG. 6 or FIG. 9, the therein disclosed grating polychromator 98 can be replaced with a scanning monochromator, not shown. It will be appreciated that with a scanning monochromator, only one fluorescence detector is required. Readout will have to be seriatim, however. This results in a less expensive instrument but at some loss of speed per analysis.

Figure 10:
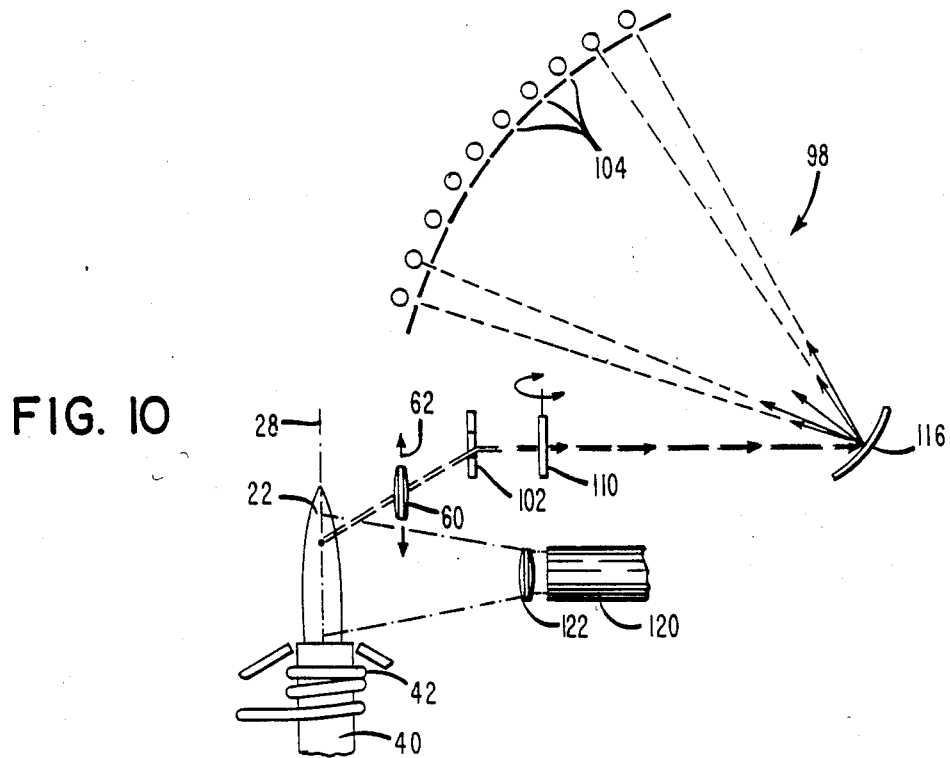
FIG. 10 is a schematic view of a sixth embodiment of a portion of the ICP-AFS instrument shown in FIG. 1.

A still further embodiment of a portion of the ICP-AFS instrument 10 is depicted in FIG. 10. The embodiment of FIG. 10 can be used in conjunction with the grating polychromator 98 disclosed in FIGS. 6 and 9 or together with a scanning monochromator, not shown but discussed above. In the embodiment of FIG. 10, in lieu of a plurality of energizers 24, be they regular or demountable hollow cathode lamps, only one broad-band energizer 120 is used. This broad-band energizer 120 is employed in conjunction with a lens 122 so as to excite simultaneously all of the elements in the sample along the axial 28 length of the plasma stream 22. Such an arrangement also helps to reduce costs in that it eliminates the requirement of a separate excitation energizer 24 for each element to be analyzed.

Other and further features of the ICP-AFS instrument 10 include a plurality of control buttons 124 and a number of gauges 126 mounted on the control panel 14 that are required for the operation of the instrument 10. Sample solutions from vials or cups, not shown, are introduced into the instrument 10 by being presented to an aspirator probe 128 conveniently located on the instrument panel 14. The probe 128 aspirates the required precise amount of the sample solution to a nebulizer mounted behind the instrument panel 14. From the nebulizer, the sample solution is introduced, via suitable tubing, to the plasma torch 40, and hence into the plasma stream 22 emanating from the torch 40. The signals measured by the respective detectors 26 (or one detector, as the case may be) are processed by a system built into the base cabinet 12 that includes time division multiplexing and intermittent modulation of the measured signals, as well as other processing electronics and power packs, which may be as disclosed in said copending application Ser. No. 152,387. The results of the fluorescence measurements are readily and quickly displayed at the CRT display 16, normally within seconds after sample aspiration.

Thus it has been shown and described an improved ICP-AFS instrument 10 designed for the multielement analysis of unknown samples, which instrument 10 satisfies the objects and advantages set forth above.

Since certain changes may be made in the present disclosure without departing from the scope of the present invention, it is intended that all matter described in the foregoing specification or shown in the accompanying drawings, be interpreted in an illustrative and not in a limiting sense.

What is claimed is:

1. A fluorescence spectrometer for multielement analysis of samples comprising:
    (a) a source for atomizing a dispersed sample along an axis;
    (b) a plurality of pairs of energizers and detectors mounted about said source, with each of said pairs for determining one of said elements;
    (c) said energizers and said detectors being each mounted on a carousel.

2. A fluorescence spectrometer for multielement analysis of samples comprising:
    (a) a source for atomizing a dispersed sample along an axis;
    (b) a plurality of demountable hollow cathode lamps mounted about said source for exciting said elements in said sample;
    (c) a plurality of detectors also mounted about said source for detecting fluorescent emission from said excited elements;
    (d) said demountable hollow cathode lamps and said detectors arranged in pairs, with each of said pairs for determining one of said elements and viewing a different segment of said source;
    (e) said demountable hollow cathode lamps continuously being flushed with an inert gas;
    (f) said source being an inductively coupled plasma movable along its said axis; and
    (g) a movable optical element mounted between said pairs and said source for permitting said pairs to view different segments of said source along its said axis.

3. A fluorescence spectrometer for multielement analysis of samples comprising:
    (a) a source for atomizing a dispersed sample along an axis;
    (b) a plurality of demountable hollow cathode lamps mounted about said source for exciting said elements in said sample;
    (c) a plurality of detectors also mounted about said source for detecting fluorescent emission from said excited elements;
    (d) said demountable hollow cathode lamps and said detectors arranged in pairs, with each of said pairs for determining one of said elements and viewing a different segment of said source;
    (e) which is a floor mounted instrument and wherein said lamps and said detectors are respectively mounted on a carousel.

* * * * *